United States Patent [19]

Ando et al.

[11] Patent Number: 5,600,022

[45] Date of Patent: Feb. 4, 1997

[54] METHOD FOR RECOVERING CHLOROMETHYL METHYL ETHER

[75] Inventors: Kiyoto Ando; Akihiko Tsukada; Hiroshi Arataki; Youichi Tamura, all of Kitakyushu, Japan

[73] Assignee: Mitsubishi Chemical Corporation, Tokyo, Japan

[21] Appl. No.: 364,727

[22] Filed: Dec. 27, 1994

[30] Foreign Application Priority Data

Dec. 27, 1993 [JP] Japan ................................. 5-347071

[51] Int. Cl.$^6$ ................................................ C07C 41/00
[52] U.S. Cl. ............................................. 568/682; 568/681
[58] Field of Search ................................. 568/682, 681

[56] References Cited

FOREIGN PATENT DOCUMENTS

| | | |
|---|---|---|
| 150332 | 8/1985 | European Pat. Off. . |
| 0327255 | 8/1989 | European Pat. Off. . |
| 942516 | 11/1963 | United Kingdom . |
| 1025635 | 4/1966 | United Kingdom . |
| 1049270 | 11/1966 | United Kingdom . |
| WO87/04369 | 7/1987 | WIPO . |

*Primary Examiner*—Gary Geist
*Assistant Examiner*—Dwayne C. Jones
*Attorney, Agent, or Firm*—Oblon, Spivak, McClelland, Maier & Neustadt, P.C.

[57] ABSTRACT

In a reaction for introducing chloromethyl groups into an aromatic crosslinked copolymer by reacting chloromethyl methyl ether to the aromatic crosslinked copolymer in the presence of a chloromethylation reaction catalyst, a method for recovering chloromethyl methyl ether from the reaction mixture, which comprises the following steps 1) a step of adding to the reaction mixture an aqueous acid solution which is capable of dissolving the chloromethylation reaction catalyst without decomposing chloromethyl methyl ether, and an extraction solvent which is inert to and miscible with chloromethyl methyl ether and which is capable of swelling the chloromethylated aromatic crosslinked copolymer, 2) a step of contacting hydrogen chloride gas to the reaction mixture and the extract solution from the step 1 to convert decomposition products of chloromethyl methyl ether, to chloromethyl methyl ether, 3) a step of separating the resulting mixture from the step 2 into an extraction solvent layer containing chloromethyl methyl ether and an acid-containing aqueous layer, and 4) a step of separating the chloromethyl methyl ether from the extraction solvent layer separated in the step 3.

10 Claims, No Drawings

METHOD FOR RECOVERING CHLOROMETHYL METHYL ETHER

BACKGROUND OF THE INVENTION

1. Field of the Invention

The present invention relates to a process for producing a chloromethylated aromatic crosslinked copolymer useful as an intermediate for the production of an anion exchange resin. More particularly, it relates to a method for efficiently recovering chloromethyl methyl ether from a reaction mixture, when a styrene-type crosslinked copolymer is chloromethylated, so that the chloromethylation reaction can be economically carried out.

2. Discussion of Background

An anion exchange resin is produced usually by introducing chloromethyl groups to an aromatic crosslinked copolymer by means of chloromethyl methyl ether and a Lewis acid catalyst, followed by amination with various amines.

In the reaction for introducing chloromethyl groups, it is common to employ an excess amount of chloromethyl methyl ether to accomplish the desired degree of introduction. This excess amount of chloromethyl methyl ether is decomposed with water or an alcohol for treatment after the reaction. Therefore, such a method is not desirable from the economical viewpoint.

On the other hand, as a method for recovering such an excess amount of chloromethyl methyl ether, East German Patents No. 27643 and 113107 disclose a method wherein after a chloromethylation reaction, the chloromethylated polymer is separated by filtration from the reaction solution, and then chloromethyl methyl ether is recovered from the reaction solution. However, chloromethyl methyl ether is a solvent which swells the chloromethylated polymer very well. Accordingly, a substantial amount of chloromethyl methyl ether remains in the chloromethylated polymer thus separated by filtration. In these patents, the chloromethylated polymer separated by filtration, is washed with methanol, whereby the chloromethyl methyl ether remaining in the chloromethylated polymer is decomposed and removed. Such a method is not an efficient recovery method.

Rumanian Patent No. 79140 and Japanese Examined Patent Publication No. 61204/1987 disclose a method wherein concentrated hydrochloric acid, or concentrated hydrochloric acid and formaldehyde as a starting material for chloromethyl methyl ether, are added after completion of a chloromethylation reaction, and then chloromethyl methyl ether is recovered by distillation. By this recovery method, it is possible to recover chloromethyl methyl ether contained in the chloromethylated polymer, and the recovery rate is fairly high. However, when chloromethyl methyl ether is distilled under heating in the presence of concentrated hydrochloric acid, the chloromethyl methyl ether or its decomposition products such as formaldehyde and methanol which are convertible again to chloromethyl methyl ether, will undergo side reactions by the heating to form methyl formate or methyl chloride, thus leading to a recovery loss. Therefore, such a method is not fully satisfactory as a recovery method. A similar recovery method is disclosed also in European Patent No. 0327255.

SUMMARY OF THE INVENTION

It is an object of the present invention to provide a method for recovering chloromethyl methyl ether, free from the above-mentioned problems. More specifically, it is an object of the present invention to provide a method wherein in a chloromethylation reaction for producing a chloromethylated aromatic crosslinked copolymer useful as an intermediate for an anion exchange resin, chloromethyl methyl ether remaining in the reaction solution after the reaction and in the chloromethylated aromatic crosslinked copolymer, is recovered, and the recovery is efficiently carried out while suppressing side reactions at the time of the recovery.

Namely, the present invention provides, in a reaction for introducing chloromethyl groups into an aromatic crosslinked copolymer by reacting chloromethyl methyl ether to the aromatic crosslinked copolymer in the presence of a chloromethylation reaction catalyst, a method for recovering chloromethyl methyl ether from the reaction mixture, which comprises the following steps:

1) a step of adding to the reaction mixture an aqueous acid solution which is capable of dissolving the chloromethylation reaction catalyst without decomposing chloromethyl methyl ether, and an extraction solvent which is inert to and miscible with chloromethyl methyl ether and which is capable of swelling the chloromethylated aromatic crosslinked copolymer, 2) a step of contacting hydrogen chloride gas to the reaction mixture and the extract solution from the step 1 to convert decomposition products of chloromethyl methyl ether, to chloromethyl methyl ether, 3) a step of separating the resulting mixture from the step 2 into an extraction solvent layer containing chloromethyl methyl ether and an acid-containing aqueous layer, and 4) a step of separating the chloromethyl methyl ether from the extraction solvent layer separated in the step 3.

PREFERRED EMBODIMENTS OF THE INVENTION

Now, the present invention will be described in detail with reference to the preferred embodiments.

Introduction of chloromethyl groups into an aromatic crosslinked copolymer of the present invention is carried out by a conventional method wherein chloromethyl methyl ether is reacted to the aromatic crosslinked copolymer in the presence of a chloromethylation catalyst.

The aromatic crosslinked copolymer may, for example, be a copolymer of a styrene-type monomer such as styrene, α-methylstyrene or vinyltoluene, with an aromatic polyvinyl monomer such as divinylbenzene or trivinylbenzene. Particularly preferred is a copolymer of styrene with divinylbenzene.

The proportions of the styrene-type monomer and the aromatic polyvinyl monomer are not particularly limited and may suitably be determined depending upon the particular use. However, usually the aromatic polyvinyl monomer is used in an amount of from 1 to 40 mols per 100 mols of the styrene-type monomer.

The aromatic crosslinked copolymer may be not only a common gel-type polymer but also a porous polymer (porous type or macroreticular type).

When chloromethyl methyl ether is reacted to the aromatic crosslinked copolymer, the chloromethyl methyl ether is used excessively relative to the copolymer. Usually, it is used at least 1.0, preferable from 1.5 to 10 times by weight relative to the copolymer. If it is too small than this range, no adequate reaction will be carried out. On the other hand, if it is too much, recovery treatment after the reaction will be troublesome. At the time of the reaction, it is preferred that the aromatic crosslinked copolymer is sufficiently impregnated and swelled with chloromethyl methyl ether and then contacted with the chloromethylation catalyst.

The present invention is effective also in a case where a solvent which is capable of swelling the copolymer and which is inert to the chloromethylation reaction, is added at the time of reacting chloromethyl methyl ether to the aromatic crosslinked copolymer. The solvent which is capable of swelling the copolymer and which is inert to the chloromethylation reaction, may, for example, be a halogenated hydrocarbon such as dichloromethane or 1,2-dichloroethane. To facilitate recovery of chloromethyl methyl ether or the solvent after the subsequent extraction with a solvent, it is preferred to employ the same solvent as the solvent for extraction after the reaction. The purpose of adding the solvent for the chloromethylation reaction is to reduce the amount of chloromethyl methyl ether to be used, and the amount of its addition is not particularly limited so long as a desired quantity of chloromethyl groups can be introduced, but it is used usually from 0.5 to 3 times by weight relative to the copolymer.

A typical catalyst as the chloromethylation catalyst is a Lewis acid, such as zinc chloride, aluminum chloride or tin chloride. Such a chloromethylation catalyst is used usually in an amount of from 1 to 500 wt %, preferably from 10 to 300 wt %, relative to the copolymer.

The reaction temperature is usually from 20° to 150° C., preferably from 30° to 100° C., and the reaction time is usually from 1 to 20 hours.

In the present invention, after completion of the chloromethylation reaction, an acid which is capable of dissolving the chloromethylation catalyst without decomposing chloromethyl methyl ether, is firstly added to the reaction mixture. This is intended to extract and remove the reaction catalyst, and the acid is added in the form of an aqueous solution. As the aqueous acid solution to be added, an aqueous acid solution having a relatively high concentration, such as an aqueous hydrochloric acid solution having a concentration of from 25 to 35 wt %, preferably from 30 to 35 wt %, or an aqueous sulfuric acid solution having a concentration of from 40 to 70 wt %, preferably from 50 to 60 wt %, may, for example, be mentioned. Further, from the operational viewpoint, it is advantageous to use hydrochloric acid as the acid, since in the subsequent step, the decomposition products of chloromethyl methyl ether will be contacted with hydrogen chloride gas for effective recovery.

The amount of this aqueous acid solution varies depending upon the type and the amount of the chloromethylation reaction catalyst, but it is usually at least 50 wt %, relative to the amount of the chloromethylation reaction catalyst, preferably from 100 to 1,000 wt %, relative to the amount of the chloromethylation reaction catalyst.

Further, to the reaction mixture having the aqueous acid solution added thereto, an extraction solvent which is inert to and miscible with chloromethyl methyl ether and which is capable of swelling the chloromethylated aromatic crosslinked copolymer (hereinafter referred to simply as a chloromethylated polymer), is added to extract chloromethyl methyl ether in the reaction mixture and in the chloromethylated polymer and to extract decomposition products of chloromethyl methyl ether, which can be converted again to chloromethyl methyl ether, into the extraction solvent.

According to the present invention, by this extraction treatment, chloromethyl methyl ether remaining in the reaction mixture and in the chloromethylated polymer can be quantitatively recovered without heating i.e. at a temperature of less than 100° C., preferably at most 50° C. Namely, the conventional step of heating in the presence of concentrated hydrochloric acid and the chloromethylation reaction catalyst, such as removal of chloromethyl methyl ether by distillation, can be omitted, whereby side reactions of the decomposition products of chloromethyl methyl ether i.e. formalin and methanol which can be converted again to chloromethyl methyl ether, as shown below, can be suppressed. Accordingly, the recovery efficiency of chloromethyl methyl ether can be improved, and at the same time, it will be unnecessary to treat undesired products which will otherwise be produced by the side reactions.

$CH_3OCH_2Cl+H_2O \leftarrow\rightarrow CH_3OH+HCHO+HCl$ (Chloromethyl methyl ether)

Side reactions $2HCHO \rightarrow HCOOCH_3$ $CH_3OH+HCl \rightarrow CH_3Cl+H_2O$ The extraction solvent which is inert to and miscible with chloromethyl methyl ether and which is capable of swelling the chloromethylated polymer, may, for example, be a halogenated hydrocarbon such as dichloromethane, 1,2-dichloroethane, perchloroethane, perchloroethylene, chlorobenzene, bromobenzene or o-dichlorobenzene, or an aromatic hydrocarbon such as benzene, toluene or xylene.

The amount of the extraction solvent is not particularly limited, so long as it is an amount sufficient for extraction of chloromethyl methyl ether. However, it is usually within a range of from 100 to 2,000 wt %, preferably from 200 to 500 wt %, relative to the chloromethylated polymer.

In the present invention, the aqueous acid solution and the extraction solvent are added to the reaction mixture. The extraction solvent may be added after addition of the aqueous acid solution. Otherwise, they may be added simultaneously. However, it is preferred to sequentially add the aqueous acid solution and the extraction solvent.

As the method for extraction treatment, a batch system extraction method or a continuous extraction method employing an extraction column may be employed. Preferably a continuous extraction method is employed, whereby the extraction solvent can be minimized.

After the extraction treatment, the chloromethylated polymer is separated by e.g. filtration from the mixture comprising the reaction mixture, the aqueous acid solution and the extraction solvent, to obtain a reaction mixture comprising mainly the resulting reaction mixture (having the chloromethylated polymer removed) and the aqueous acid solution, and an extract solution comprising mainly the extraction solvent and the extracted product such as chloromethyl methyl ether.

In the continuous extraction method, the mixture comprising the reaction mixture and the aqueous acid solution may be transferred to a column, and the extraction solvent is passed therethrough to obtain the above-mentioned reaction mixture and the extract solution and at the same time to separate the chloromethylated polymer.

The reaction mixture and the extract solution are usually recovered together. This recovered mixture comprising the reaction mixture and the extract solution is separated into two layers i.e. an aqueous layer containing the acid and a layer of the extraction solvent. These layers are thoroughly stirred and contacted with hydrogen chloride gas in a mixed state of the two layers to convert substances convertible to chloromethyl methyl ether among decomposition products of chloromethyl methyl ether remaining in the mixture, to chloromethyl methyl ether.

In the present invention, hydrogen chloride gas is contacted in the state where two layers i.e. the aqueous layer containing an acid such as hydrochloric acid and the extraction solvent layer, are present, whereby the decomposition products of chloromethyl methyl ether, which are convertible to chloromethyl methyl ether and which are substantially distributed also in the aqueous layer, can be effectively recovered in the form of chloromethyl methyl ether, and the recovery efficiency is increased.

It is per se known that the decomposition products of chloromethyl methyl ether, which are convertible to chloromethyl methyl ether, are contacted to hydrogen chloride gas to convert them to chloromethyl methyl ether, as disclosed, for example, in the above-mentioned Rumanian Patent or Japanese Examined Patent Publication No. 61204/1987.

The amount of the hydrogen chloride gas to be contacted, is not particularly limited so long as it is an amount sufficient to convert the recovered decomposition products of chloromethyl methyl ether, which are convertible to chloromethyl methyl ether, to chloromethyl methyl ether. However, it is usually within a range of from 100 to 1,000 mol %, preferably from 150 to 500 mol %, relative to the substances which are convertible to chloromethyl methyl ether, which are present.

After converting the decomposition products of chloromethyl methyl ether, which are convertible to chloromethyl methyl ether, to chloromethyl methyl ether, by the contact with hydrogen chloride gas, the mixed solution is separated into the extraction solvent layer containing chloromethyl methyl ether and the aqueous hydrochloric acid layer containing the chloromethylation catalyst, and these layers will be separated by an operation of e.g. liquid separation. Specifically, the mixed solution may be introduced into a batch system separation tank and permitted to stay there for a predetermined period of time to let it separate completely, whereupon from the bottom of the tank, the heavy liquid and then the light liquid may be withdrawn into the respective prescribed storage tanks.

The extraction solvent layer containing chloromethyl methyl ether, thus obtained by the liquid separation, will then be separated into the extraction solvent and the chloromethyl methyl ether for recovery. For this separation and recovery step, any operation may be employed so long as it is capable of separating the extraction solvent and the chloromethyl methyl ether. For example, distillation, solvent extraction, separation by membranes or chromatographic separation may be mentioned. However, it is usually preferred to conduct the separation by distillation. The distillation is usually conducted by a batch system distillation under atmospheric pressure (plate number: 10 plates, R: 5, column top temperature: 60° C.). By the distillation, chloromethyl methyl ether will be heated. However, since the aqueous hydrochloric acid layer containing the chloromethylation catalyst has previously been separated and removed, no substantial side reaction such as conversion of methanol formed under heating in the presence of hydrochloric acid, to methyl chloride, will take place.

According to the method of the present invention, not only chloromethyl methyl ether remaining in the reaction mixture after completion of the chloromethylation reaction, but also chloromethyl methyl ether remaining in the chloromethylated polymer, can be recovered, and at the same time, substantially all the amount of the decomposition products of chloromethyl methyl ether, which are convertible to chloromethyl methyl ether, can be recovered. Besides, side reactions at the time of the recovery can be suppressed, and chloromethyl methyl ether of high purity can be recovered at a high recovery rate. Thus, the method of the present invention is very useful as an industrial method.

Now, the present invention will be described in further detail with reference to Examples. However, it should be understood that the present invention is by no means restricted to such specific Examples.

EXAMPLE 1

Into a 1 l three-necked flask equipped with a stirrer and a reflux condenser, 100 g of a styrene-divinylbenzene crosslinked copolymer (a gel-type copolymer having a divinylbenzene content of 6.5 wt %) and 270 g of chloromethyl methyl ether were introduced and stirred at room temperature for 3 hours to swell the copolymer. Then, 42 g of zinc chloride was added, and a chloromethylation reaction was carried out at 50° C. for 8 hours. After completion of the reaction, the reaction mixture was cooled to room temperature, and 300 g of a 35 wt % hydrochloric acid aqueous solution was dropwise added thereto over a period of 3 hours. After completion of the dropwise addition, the reaction solution was transferred to a column having an inner diameter of 50 mm and a height of 500 mm, and 350 g of toluene was passed from the top at SV1 to conduct separation and recovery of the reaction mixture and extraction and recovery of chloromethyl methyl ether from the chloromethylated copolymer.

The separated and recovered reaction mixture and the extract solution were mixed and introduced into a 1 l three-necked flask equipped with a reflux condenser and a supply tube for introducing hydrogen chloride gas into the liquid. Then, 60 g of hydrogen chloride gas was introduced into the reaction solution with stirring at room temperature at a rate of 30 g/hr over a period of two hours, to convert decomposition products of chloromethyl methyl ether, which are convertible to chloromethyl methyl ether, to chloromethyl methyl ether.

After introducing the hydrogen chloride gas, the mixture was separated by means of a 2 l separating funnel into an aqueous hydrochloric acid layer containing zinc chloride as the lower layer and an extract solution layer containing chloromethyl methyl ether. This extract solution layer was analyzed, whereby it was found to contain 151.5 g of chloromethyl methyl ether. This amount of chloromethyl methyl ether was 56% of chloromethyl methyl ether used for the reaction.

Chloromethyl methyl ether mixed with toluene was introduced into a 1 l flask equipped with a distillation column having an inner diameter of 30 mm and a plate number of 10 plates, and toluene and chloromethyl methyl ether were separated by distillation under a condition of a reflux ratio of 5. Chloromethyl methyl ether obtained at the distillate side of the distillation was 160.6 g, and the purity of chloromethyl methyl ether (CME) was 85%. The recovered amount of chloromethyl methyl ether alone was 136.5 g, and this amount corresponded to 50.5% of chloromethyl methyl ether used for the reaction.

Comparative Example 1 (Recovery method
according to Japanese Examined Patent Publication
No. 61204/1987)

The chloromethylation reaction was conducted in the same manner as in Example 1. After the chloromethylation reaction, 250 g of 35 wt % hydrochloric acid was added to the mixture. Then, a distillation apparatus was attached to the reactor, and the mixture was heated to 98° C. under atmospheric pressure, whereby the volatile component was distilled and recovered. The distilled component was left to stand and then subjected to liquid separation into a hydrochloric acid layer and an organic layer containing chloromethyl methyl ether.

Chloromethyl methyl ether obtained by this method was 157 g, and the purity of CME was 69.1%. The recovered amount of chloromethyl methyl ether alone was 108.5 g, and this amount corresponded to 40.2% of chloromethyl methyl ether used for the reaction.

EXAMPLE 2

The operation was conducted in the same manner as in Example 1 except that instead of 300 g of 35 wt % hydrochloric acid, 60 wt % sulfuric acid was employed.

Chloromethyl methyl ether finally obtained after the distillation was 156.8 g, and the purity of CME was 86%. The recovered amount of chloromethyl methyl ether alone was 134.8 g, and this amount corresponded to 49.9% of chloromethyl methyl ether used for the reaction.

EXAMPLE 3

The operation was conducted in the same manner as in Example 1 except that 500 g of 1,2-dichloroethane was used instead of toluene as the extraction solvent.

Chloromethyl methyl ether finally obtained after the distillation was 159.2 g, and the purity of CME was 84%. The recovered amount of chloromethyl methyl ether alone was 133.7 g, and this amount corresponded to 49.5% of chloromethyl methyl ether used for the reaction.

EXAMPLE 4

Into a 1 l three-necked flask equipped with a stirrer and a reflux condenser, 100 g of a styrene-divinylbenzene crosslinked copolymer (a porous copolymer having a divinylbenzene content of 4.0 wt %), 200 g of chloromethyl methyl ether and 120 g of 1,2-dichloroethane were introduced and stirred for 3 hours at room temperature to swell the copolymer. Then, 50 g of zinc chloride was added thereto, and a chloromethylation reaction was carried out at 50° C. for 10 hours. After completion of the reaction, the reaction mixture was cooled to room temperature, and 300 g of a 35 wt % hydrochloric acid aqueous solution was dropwise added thereto over a period of 3 hours. After completion of the dropwise addition, the reaction solution was transferred to a column having an inner diameter of 50 mm and a height of 500 mm, and 250 g of 1,2-dichloroethane was passed from the top at SV1 to conduct separation and recovery of the reaction mixture and extraction and recovery of chloromethyl methyl ether from the chloromethylated copolymer.

The separated and recovered reaction mixture and the extract solution were mixed and introduced into a 1 l three-necked flask equipped with a reflux condenser and a supply tube for introducing hydrogen chloride gas into the liquid. Then, 50 g of hydrogen chloride gas was introduced into the reaction solution with stirring at room temperature at a rate of 25 g/hr over a period of two hours, to convert the decomposition products of chloromethyl methyl ether, which are convertible to chloromethyl methyl ether, to chloromethyl methyl ether.

After introducing the hydrogen chloride gas, the mixture was separated by means of a 2 l separating funnel into an aqueous hydrochloric acid layer containing zinc chloride and an extract solution layer containing chloromethyl methyl ether. This extract solution layer was analyzed, whereby it was found to contain 109.3 g of chloromethyl methyl ether and 173 g of 1,2-dichloroethane. This amount of chloromethyl methyl ether was 55% of chloromethyl methyl ether used for the reaction.

Chloromethyl methyl ether mixed with 1,2-dichloroethane was introduced into a 1 l flask equipped with a distillation column having an inner diameter of 30 mm and a plate number of 10 plates, and 1,2-dichloroethane and chloromethyl methyl ether were separated by distillation under a condition of a reflux ratio of 5. Chloromethyl methyl ether obtained at the distilled side of the distillate was 118.4 g, and the purity of chloromethyl methyl ether (CME) was 83%. The recovered amount of chloromethyl methyl ether alone was 98.3%, and this amount corresponded to 49.2% of chloromethyl methyl ether used for the reaction.

What is claimed is:

1. In a reaction for introducing chloromethyl groups into an aromatic crosslinked copolymer by reacting chloromethyl methyl ether to the aromatic crosslinked copolymer in the presence of a chloromethylation reaction catalyst, a method for recovering chloromethyl methyl ether from the reaction mixture, which comprises the following steps:

1) a step of adding to the reaction mixture an aqueous acid solution which is capable of dissolving the chloromethylation reaction catalyst without decomposing chloromethyl methyl ether, and an extraction solvent which is inert to and miscible with chloromethyl methyl ether and which is capable of swelling the chloromethylated aromatic crosslinked copolymer, 2) a step of contacting hydrogen chloride gas to the reaction mixture and the extract solution from the step 1 to convert decomposition products of chloromethyl methyl ether, to chloromethyl methyl ether, 3) a step of separating the resulting mixture from the step 2 into an extraction solvent layer containing chloromethyl methyl ether and an acid-containing aqueous layer, and 4) a step of separating the chloromethyl methyl ether from the extraction solvent layer separated in the step 3.

2. The method for recovering chloromethyl methyl ether according to claim 1, wherein the aromatic crosslinked polymer is a styrene-divinylbenzene crosslinked copolymer.

3. The method for recovering chloromethyl methyl ether according to claim 1, wherein the chloromethylation reaction catalyst is a Lewis acid.

4. The method for recovering chloromethyl methyl ether according to claim 1 or 3, wherein the aqueous acid solution which is capable of dissolving the chloromethylation reaction catalyst without decomposing chloromethyl methyl ether, is an aqueous hydrochloric acid solution having a concentration of at least 30 wt %, or an aqueous sulfuric acid solution having a concentration of from 40 to 70 wt %.

5. The method for recovering chloromethyl methyl ether according to claim 1 or 4, wherein the aqueous acid solution which is capable of dissolving the chloromethylation reaction catalyst without decomposing chloromethyl methyl ether, is added in an amount of from 100 to 1,000 wt % relative to the amount of the chloromethylation reaction catalyst.

6. The method for recovering chloromethyl methyl ether according to claim 1, wherein the solvent which is inert to chloromethyl methyl ether and which is capable of swelling the chloromethylated aromatic crosslinked copolymer, is selected from the group consisting of aromatic hydrocarbons and halogenated hydrocarbons.

7. The method for recovering chloromethyl methyl ether according to claim 1 or 6, wherein the solvent which is inert to chloromethyl methyl ether and which is capable of swelling the chloromethylated aromatic crosslinked copolymer, is added in an amount of from 100 to 2,000 wt % relative to the amount of the chloromethylated aromatic crosslinked copolymer.

8. The method for recovering chloromethyl methyl ether according to claim 1, wherein after adding the aqueous acid solution, the extraction solvent is added.

9. The method for recovering chloromethyl methyl ether according to claim 1 or 8, wherein the step 1 is carried out at a temperature of at most 50° C.

10. The method for recovering chloromethyl methyl ether according to claim 1, wherein each of the steps 1, 2 and 3 is carried out at a temperature of at most 50° C.

* * * * *